United States Patent [19]
Casavant

[11] Patent Number: 5,954,755
[45] Date of Patent: Sep. 21, 1999

[54] FACILITATED ATRIAL PACING THRESHOLD TESTING

[75] Inventor: David A. Casavant, Reading, Mass.

[73] Assignee: Medtronic, Inc., Minneapolis, Minn.

[21] Appl. No.: 08/870,326

[22] Filed: Jun. 6, 1997

[51] Int. Cl.⁶ .................................................. A61N 1/362
[52] U.S. Cl. ............................................................. 607/28
[58] Field of Search ..................... 607/28, 14, 9

[56] References Cited

U.S. PATENT DOCUMENTS

| | | | |
|---|---|---|---|
| 4,257,423 | 3/1981 | McDonald et al. | 128/419 PG |
| 4,374,382 | 2/1983 | Markowitz | 340/870.01 |
| 4,556,063 | 12/1985 | Thompson et al. | 128/419 PT |
| 5,127,404 | 7/1992 | Wyborny et al. | 128/419 |
| 5,476,487 | 12/1995 | Sholder | 607/28 |
| 5,480,414 | 1/1996 | Stroebel et al. | 607/28 |
| 5,507,782 | 4/1996 | Kieval et al. | 607/9 |
| 5,601,615 | 2/1997 | Markowitz | 607/28 |

OTHER PUBLICATIONS

Johshua M. Feuer et al Pace (vol. 13 pp1254:1259) Alternate Methods for the Determination of Atrial Capture Threshold Utilizing the Telemetred Electrogram.

*Primary Examiner*—William E. Kamm
*Assistant Examiner*—Kennedy J. Schaetzle
*Attorney, Agent, or Firm*—Harold R. Patton; Michael B. Atlass

[57] ABSTRACT

A system and methodology permit facilitated review of atrial pacing threshold testing. Primarily the system allows the ventricular rate to fall substantially below the atrial rate, preferrably to ½ the atrial pacing rate. A number of ways to accomplish this are described including forcing mode switches between ADI and DDI between beats, except where ventricular events follow atrial paces. Application of the technique and system to clinical, implant and follow up situations is described.

13 Claims, 10 Drawing Sheets

FACILITATED ATRIAL PACING THRESHOLD TESTING

FIELD OF THE INVENTION

This relates to electrical stimulation of the heart and to heart pacemakers and their capture threshold and detection functioning, especially for atrial stimulation pulse delivery, and to providing such function to assist in optimizing pacemaker function and pacemaker longevity in particular patients.

BACKGROUND

Periodic determination of pacemaker capture thresholds is important to ensure appropriate pacemaker function. A recent U.S. patent issued to Medtronic, U.S. Pat. No. 5,601,615, describes a system for detecting capture and measuring and finding stimulation thresholds for pacing. Accordingly it is incorporated by this reference in its entirety as it describes the kind of pacemaker systems that could benefit from the invention described in this instant document.

It should be recognized that numerous other capture detection methods and apparatae are described in the patent art and literature and that the teaching of this document is not limited exclusively to use in such systems are described in U.S. Pat. No. 5,601,615. However it is clear that atrial capture detection and threshold measurement is not a fully developed art and so this invention can be applied to any electrical stimulation device that is concerned with atrial capture detection and threshold detection (thresholding) used for such devices.

In patients having dual-chamber pacemakers, assessment of atrial capture thresholds often presents a unique challenge, particularly when confronted by either 1) a noisy or poor quality electrocardiogram (ECG), 2) a poorly visible isoelectric or fractionated (non discrete) P-wave, and/or 3) a concealed P-wave during high rate atrioventricular (AV) pacing. Present techniques for atrial capture detection or thresholding in such circumstances are inadequate.

Figure 6A:
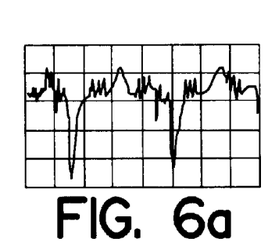
FIGS. 6a–c are illustrations of electrocardiograms (ECGs).
Figure 6B:
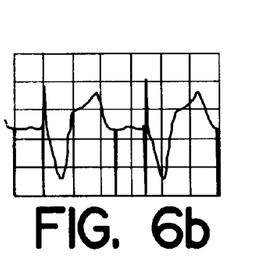
Figure 6C:
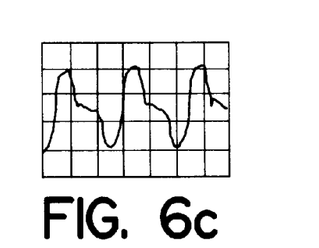

To be more specific, according to current accepted medical practice, assessment of atrial capture thresholds in dual-chamber pacemaker patients can be an oft-difficult and potentially unnerving task. In many instances, electrocardiographic visualization of atrial capture may be obscured by a noisy or poor quality ECG(electrocardiogram), a poorly visible or fractionated (non-discrete) P-wave, or concealment of the evoked P-wave in the T-wave of the preceding ventricular depolarization (This can easily be seen with reference to FIGS. 6a–c. These Figs. illustrate electrocardiograms that may be taken with surface electrodes and illustrate the obfuscation of atrial capture by a)ECG noise, b)sub optimal ECG vector, and c)concealment by preceding paced QRST complexes, respectively).

Under such circumstances, present methods for improving atrial capture assessment in clinical practice include replacing the programmer ECG electrodes, repositioning the programmer ECG electrodes, and/or resizing the ECG display. In many instances, connecting the patient to a different ECG monitor is the best available solution, but even this is not always adequate. If the attending physician is comfortable with alternatives involving reprogramming the pacemaker to assist in determining atrial thresholds and capture, the physician may additionally respond to atrial capture uncertainty by extending the paced AV interval or changing the test mode to AAI. Manual triggering of hand/eye timed pacing pulses through a PSA (pacing system analyzer) is not practicable.

In patients having sinus bradycardia and intact A-V conduction, the task of measuring atrial capture thresholds can be greatly facilitated using deductive reasoning. An assumption of atrial capture can be inferred by observing the ventricular response to atrial overdrive pacing. Taking this assumption, direct observation of atrial capture on the electrocardiogram (ECG) can be considered redundant. Capture is apparent in FIG. 7 by observing the ventricular heart rate response to overdrive AAI (or AOO) pacing. A sudden decrease in ventricular heart rate to the underlying sinus rate indicates loss of atrial capture. This indirect assessment of atrial capture threshold is made by observing a loss of atrial capture (LOAC) by a sudden drop in the ventricular rate, here illustrated as a missing QRST complex at the LOAC indicator point in FIG. 7.

Figures 7, 8:
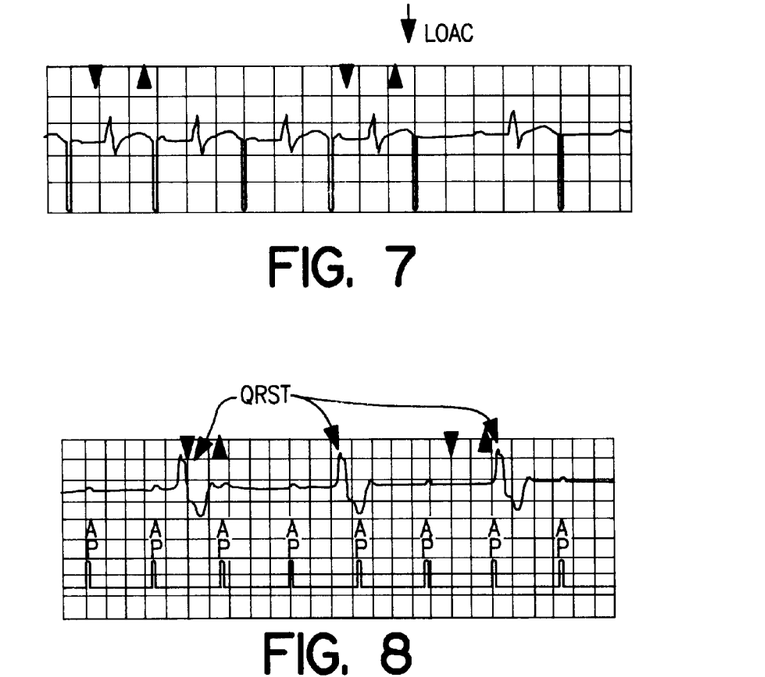
FIG. 7 illustrates another ECG.
FIG. 8 illustrates another ECG and a temporally coincident marker channel recording.

In patients with complete heart block and a slow ventricular escape rhythm, AAI pacing can facilitate visualization of atrial capture determination by extending ECG isoelectric time. This is illustrated In FIG. 8 where the ventricular rhythm (temporal linear spacing of QRST complexes) is unrelated to the AP (atrial pace) markers on the electrogram.

Caution is important in applying this AAI based technique, since pacemaker patients are prone to asystole and often have significant symptoms upon sudden cessation of ventricular pacing. Brady induced ventricular tachyarrhythmias can also be a concern in some patients, i.e. long QT syndrome). Because of the risks involved, less experienced clinicians are often reluctant to attempt to measure atrial thresholds using the AAI mode, and often forego this opportunity for threshold adjustment altogether, preferring instead to merely set the atrial stimulation pulse at or near the maximum energy level and thus shorten the potential life of the pacemaker because of its limited battery capacity.

Figure 9:
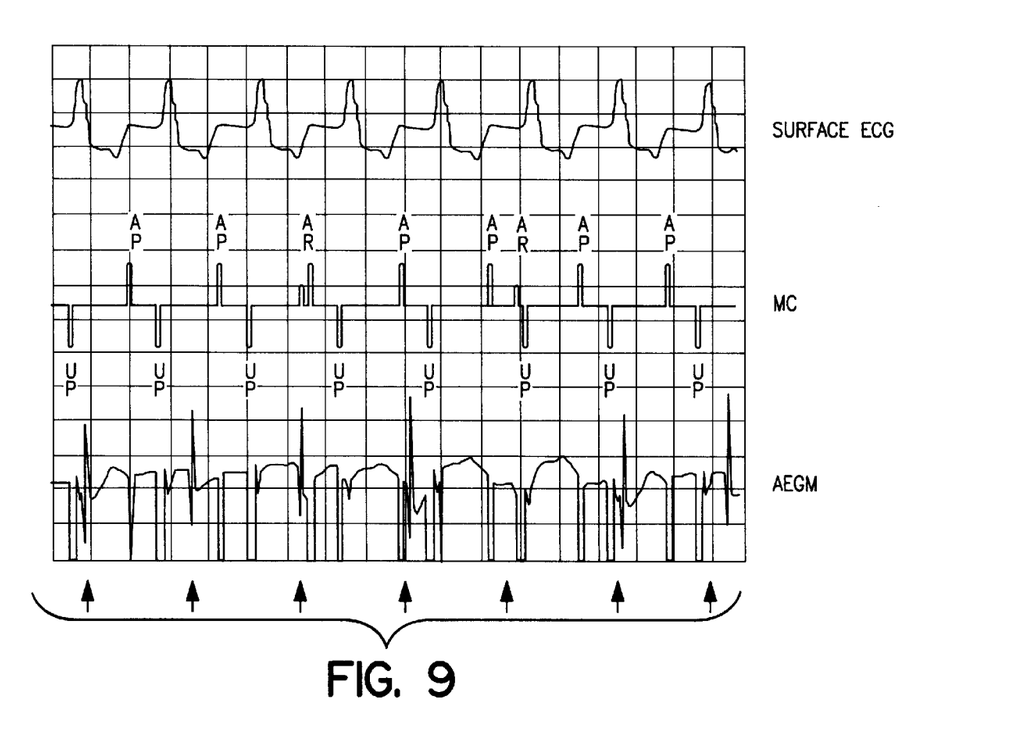
FIG. 9 illustrates a surface ECG and a temporally coincident marker channel recording and a temporary coincident intracardiac atrial electrogram (AEGM).

An alternate method to indirectly assess atrial capture while providing ventricular support involves monitoring the pacemaker's telemetered intracardiac atrial electrogram (AEGM) signals and/or marker channel. This method is described by Feuer J M, Florio J, and Shandling A H in an article titled: "Alternate methods for the determination of atrial capture threshold utilizing the telemetered intracardiac electrogram." PACE 1990, 13: 1254–1260. In this method, loss of atrial capture is inferred by the appearance of native A-waves on the AEGM, or atrial sense (AS) and/or atrial refractory sense (AR) markers on the pacemaker marker channel. This is illustrated in FIG. 9 in which the breakthrough of native A-waves can be seen on the AEGM (atrioelectrogram). In this figure the marker channel also provides evidence of atrial senses as AS or AR markers. Note the high degree of atrial non-sensing by the pacemaker due to atrial blanking periods. Native A-waves are marked in FIG. 9 with an up arrow.

Additionally, it should be noted that in the clinical setting native sinus heart rates are likely to be elevated by patient anxiety, and high heart rates are common in younger and older persons, and elevated rates over 100 bpm are commonplace in pediatric or elderly patients with congestive heart failure, thus making the provision of additional isoelectric time made available by the invention described below for visualization of LOAC more universally useful.

SUMMARY

The invention herein provides for a pacing algorithm, and a device and system to implement it that facilitates the task of measuring atrial pacing thresholds and determining atrial capture. The algorithm checks for intact conduction, and in its presence, the measurement is executed in an ADI pacing mode. Otherwise the measurement is performed using 2:1 atrioventricular pacing, thereby allowing overdrive pacing of relatively fast sinus rates (i.e. >90 bpm) while simultaneously extending ECG isoelectric time. Importantly, the algorithm is also useful for pacemaker based automatic atrial threshold determination testing although its first applications are in the clinical follow-up setting and at implant.

DETAILED DESCRIPTION OF THE PREFERRED EMBODIMENTS.

In accordance with a first aspect of the invention, the inventive apparatus and methods are incorporated into a dual chamber implantable pulse generator (IPG) as described in the following FIGS. 1–9, particularly for use with patient's having intact and regular AV conduction or first degree AV block. For patients with more severe heart block or other conditions a second aspect is also described and illustrated. It is to be understood that the inventive concepts described herein are not limited to use in a dual chamber pacer exactly as described but only as limited by the claims. The engineer of ordinary skill in these arts may apply this invention to any device needing atrial capture assurance and remain within the scope of the claimed invention. In a further aspect of the invention, an algorithm is set forth in FIG. 18 for making threshold measurements in a single chamber pacemaker or in a single chamber of a dual chamber pacemaker, particularly for patients only needing single chamber pacing or lacking intact, regular AV conduction. The following detailed description of a multi-programmable, rate responsive, dual chamber IPG and remote programmer provides a preferred mode in which either or both aspects of the invention may be incorporated. It will be understood that the single chamber pacemaker or pacing modes would selectively incorporate features of the particularly described IPG and programmer architecture as necessary.

PART I. DESCRIPTION OF THE IPG AND LEADS.

Figure 1:
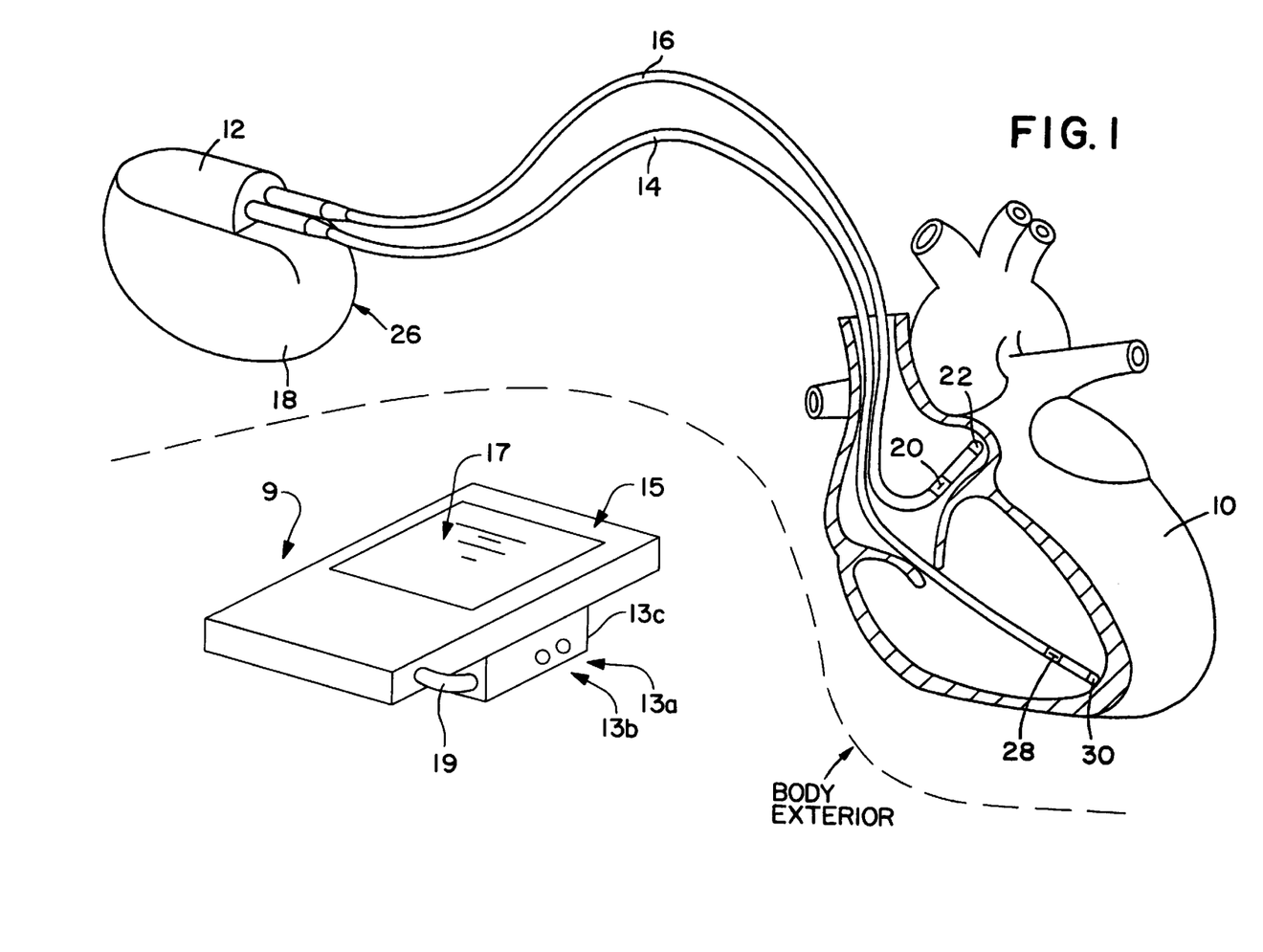
FIG. 1 is an illustration of a dual chamber pacemaker according to the present invention in conjunction with an associated set of cardiac pacing leads, illustrated as located in a cutaway view of a human heart; also in FIG. 1 is a programmable device for use with this invention outside the body.
Figure 2:
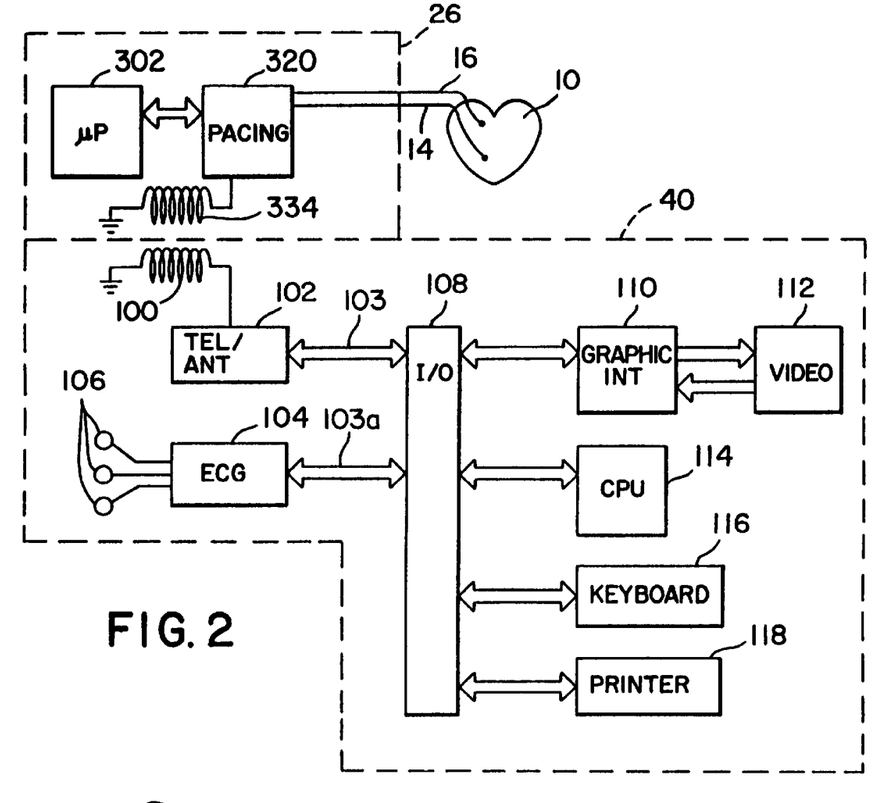
FIG. 2 is a functional block diagram of the dual chamber pacemaker illustrated in FIG. 1 in conjunction with an external programmer/monitoring unit, for use in performing the atrial capture detection and auto threshold setting functions of the present invention.
Figure 3:
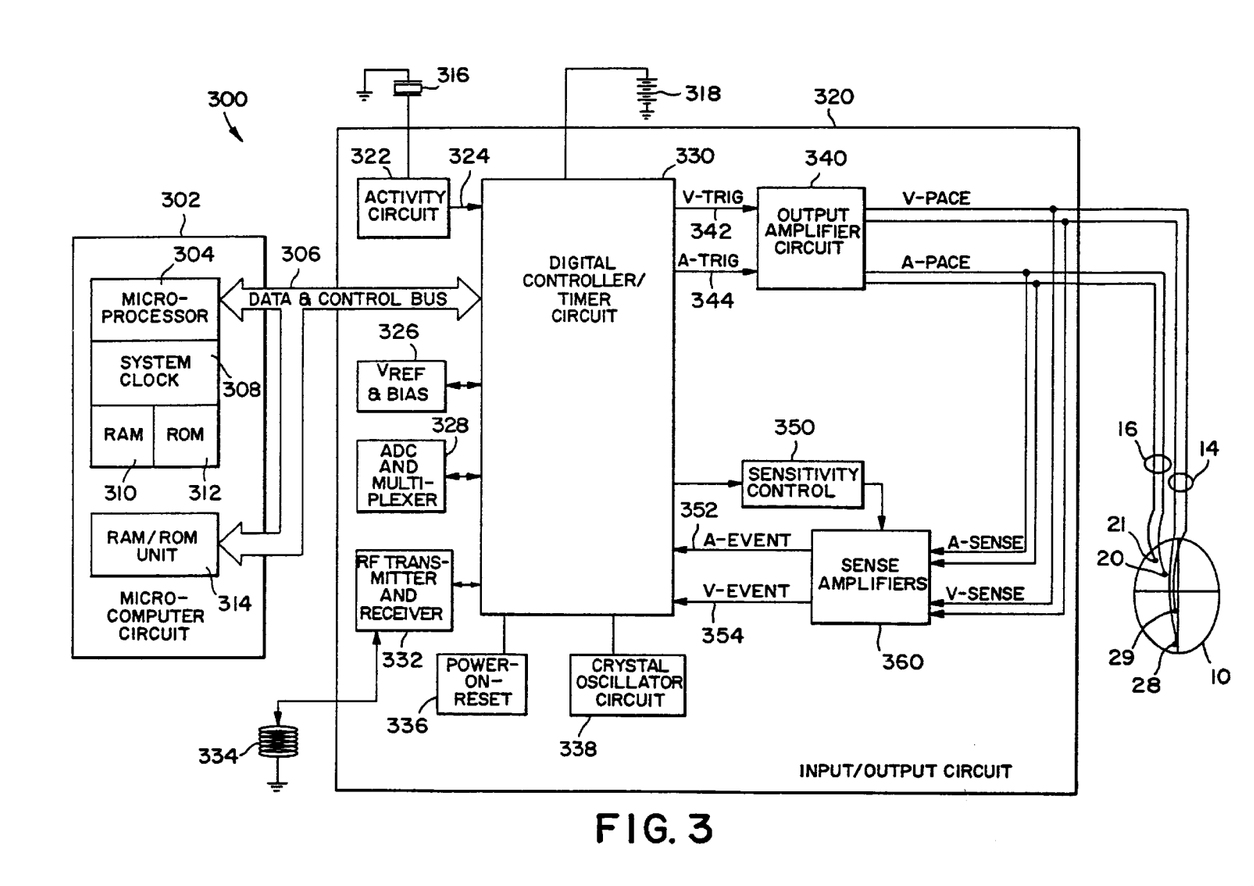
FIG. 3 is a block diagram of a dual chamber pacemaker illustrated in FIGS. 1 and 2, illustrating the functional components of the device for use in the invention in more detail.
Figure 4:
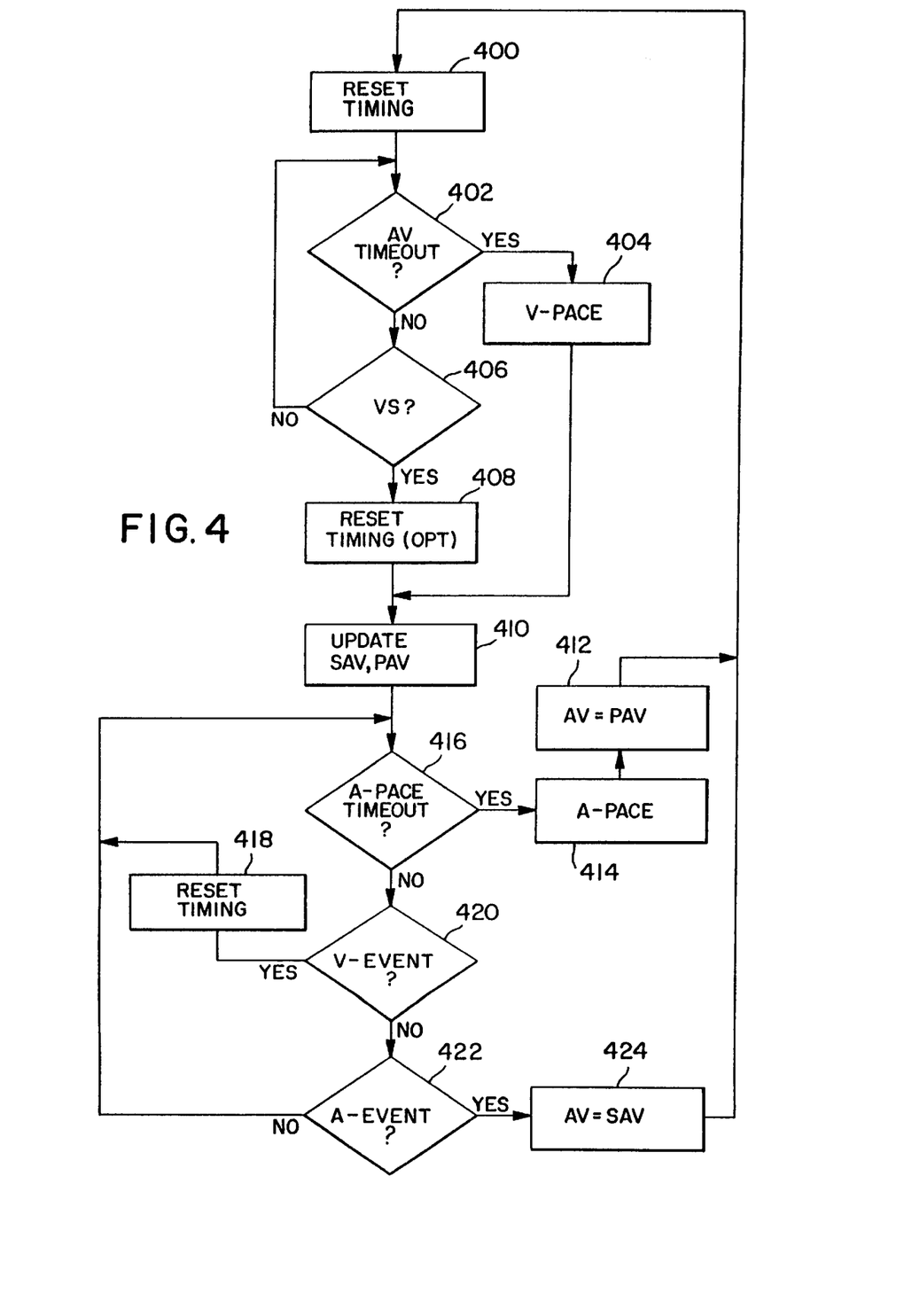
FIG. 4 is a flow chart of the overall operation of a device such as the pacemaker of FIGS. 1–3.

FIG. 1 illustrates the external configuration of a dual chamber IPG 26, which is provided with a hermetically sealed enclosure 18, typically fabricated of biocompatible metal such as Titanium. Mounted to the top of the enclosure 18 is a connector block assembly 12, which receives electrical connectors located on the proximal ends of leads 14 and 16. The combination of the leads 14 and 16 and the IPG 26 constitute an implantable pacemaker. FIGS. 1–3 and related FIG. 4 are described in U.S. Pat. No. 5,507,782, issued Apr. 16, 1996, entitled METHOD AND APPARATUS FOR DUAL CHAMBER CARDIAC PACING which application is hereby incorporated by reference.

Lead 16 is an atrial bipolar pacing lead, carrying two electrodes 20 and 22. Electrodes 20 and 22 are used both to sense atrial depolarizations (P-waves) and to deliver atrial pacing pulses. Atrial pacing pulses may be delivered between electrodes 20 and 22 in a bipolar pacing mode or between electrode 22 and the housing 18 of the IPG 26 in a unipolar pacing mode. Sensing of P-waves may occur between electrode 20 and electrode 22 in a bipolar sensing mode or between either of electrode 20 and 22 and the housing 18 of the IPG 26 in a unipolar sensing mode, all in accord with common practice in the art.

Similarly, lead 14 represents a ventricular bipolar pacing lead, carrying two electrodes 28 and 30. Similarly to atrial lead 16, electrodes 28 and 30 are used to sense and pace the ventricle in which they are located. Bipolar ventricular pacing may be accomplished between electrodes 30 and 28 or unipolar ventricular pacing may be accomplished between electrode 30 and the conductive housing 18 of IPG 26. Sensing of ventricular depolarizations or R-waves may be accomplished between electrodes 30 and 28 in a bipolar sensing mode or between either of electrodes 30 and 28 and the housing 18 of the IPG 26 in a unipolar sensing mode, all of which again in common practice in the art.

The IPG 26 preferably operates in a DDD or DDDR pacing mode, wherein pacing pulses are delivered to both atrium and ventricle and wherein sensed atrial and ventricular depolarizations are both effective to inhibit delivery of the next scheduled pacing pulse in the chamber in which they are detected. The atrial and ventricular capture detection from the ventricular electrodes afforded by the present invention is believed optimally practiced in a pacemaker operating in the DDD, DDI, DVI, DDDR, DVIR and DDIR pacing modes.

FIG. 1 additionally includes an illustration of a programmer or pacing system analyzer(PSA) 9 complete with an analog signal converting unit adapter 13c for connecting leads like 14 and 16 to the PSA 9 after converting their analog values to digital signals and forwarding the digital signals over a connector like serial connection line 19 and receiving digital signals back across line 19 to produce appropriate analog output. This analog output can be the pacing pulses used for testing the leads separately from their use with a pacemaker unit to be next connected to the same leads. In the programmer/PSA 9, illustrated for this embodiment, the intelligence required for running a digital program to prompt the delivery of signals and for sensing heart signals in accord with this invention may be accomplished by current computing devices such as laptop computers of various types or the so-called palm tops, like the Newton Messagepads(TM). All that is required is some timing and coordination digital signals to a converter device like 13c. The device 13c must in turn be able to generate and send electrical pulses of increasing or decreasing energies on demand, so as to function together with the main body of the PSA 9, 15 as a temporary pacemaker. The screen of a palmtop computer is the common interface for control by the human operator, using a touch sensitive surface 17 with a stylus or finger (not shown). If the temporary programmer/PSA is a laptop or other computer keyboard interface and other devices for control are well known ad may be employed.

It is known to control IPG's such as IPG 26 through telemetric RF or magnetic or other interface to set operating modes, and such a standard programmer device could be used as well. In FIG. 2 such a device could be illustrated with the block diagram represented by the numeral 40 in that Figure.

FIG. 2 illustrates the IPG 26 in block diagram form, coupled to a human heart 10 through the leads 14, 16, in conjunction with an external programmer 40 corresponding to those typically employed to program modern, multi-programmable implantable pacemakers. Within the housing of the IPG 26 are located the pacing circuitry 320, which includes circuitry performing all of the basic timing, stimulation and sensing functions of a DDD or DDDR cardiac pacemaker, and a microcomputer circuit 302, which controls the timing intervals provided by the pacing circuitry 320. Pacing circuitry 320 also includes a bidirectional telemetry circuit coupled to an antenna 334, allowing transmission of information from external programmer 40 into the IPG 26 to modify its parameters and allowing transmission of information from the IPG 26 to the external programmer 40, again generally corresponding to telemetry and programming systems presently existing in commercially marketed multi-programmable implantable pacemakers.

The programmer 40 also includes a telemetry antenna 100 coupled to a telemetry/antenna driver circuit 102 which serves to demodulate telemetry signals received from antenna 334 of the IPG 26, and to apply them in parallel or serial digital format to input/output (I/0) unit 108. The telemetry signals in turn may be applied to a video monitor 112, via graphic interface 110, and/or provided to central processing unit 114 and/or printer 118. Microprocessor 114 controls the operation of the programmer 40 and is responsive to physician entered commands via keyboard 116, for controlling programming signals sent to the IPG 26 and operation of the video display 112 and printer 118. Also illustrated in FIG. 2 is an ECG interface 104 coupled to three ECG electrodes 106 which are intended to be placed upon the patient's body. ECG interface 104 provides sensed electrograms to input/output device 108, where they in turn may be provided to the video display 112, the central processing unit 114 or the printer 118. Presently we can provide such programmer functionality by substituting a programming head for device connector 13c and using the palmtop 15 for the other functions of the device 40 of FIG. 2. The bus connections 103 and/or 103a would operate through line 19, were such substitution made.

FIG. 3 is a more detailed functional block diagram of the pacemaker illustrated in FIG. 1 and 2, as connected to a human heart 10. The combined IPG circuit 300 illustrated is all located within the conductive housing 18 of the IPG 26 as illustrated in FIG. 1. The bipolar leads 14 and 16 are illustrated schematically as coupled directly to the input/output circuit 320. However, in the actual implantable device they would, of course, be coupled by means of removable electrical connectors inserted in the connector block 12 illustrated in FIG. 1.

The IPG circuit 300 is divided generally into a microcomputer circuit 302 and a pacing circuit 320. An output amplifier circuit 340 includes a ventricular pulse generator circuit coupled to the ventricle of the heart 10 by means of electrodes 30 and 28 on lead 14 as well as an atrial pulse generator circuit coupled to the atrium of heart 10 by means of atrial electrodes 20 and 22, located on lead 16. Similarly, sense amplifier circuit 360 includes atrial and ventricular sense amplifiers coupled to the atrium and ventricle, respectively, by means of leads 14 and 16. The output circuit 340 and sense amplifier circuit 360 may contain pulse generators and sense amplifiers corresponding to any of those presently employed in commercially marketed cardiac pacemakers. For purposes of explaining the present invention, it will be assumed that the atrial electrodes 20, 22 and the ventricular electrodes 28, 30 are coupled to the atrial and ventricular sense amplifiers and pulse generators, respectively, for pacing and sensing in the bipolar mode.

Sensed atrial depolarizations or P-waves that are confirmed by the atrial sense amplifier (A-event) in response to an A-sense are communicated to the digital controller/timer circuit 330 on A-event line 352. Similarly, ventricular depolarizations or R-waves that are confirmed by the ventricular sense amplifier (V-event) in response to a V-sense are communicated to the digital controller/timer circuit 330 on V-event line 354. In order to trigger generation of a ventricular pacing or V-pace pulse, digital controller/timer circuit 330 generates a trigger signal on V-trig line 342. Similarly, in order to trigger an atrial pacing or A-pace pulse, digital controller/timer circuit 330 generates a trigger pulse on A-trig line 344.

Control of timing and other functions within the pacing circuit 320 is provided by digital controller/timer circuit 330, which includes a set of timers and associated logic. Digital controller/timer circuit 330 defines the basic pacing or escape interval, which may take the form of an A—A escape interval initiated on atrial sensing (A-event) or pacing (A-pace) and triggering atrial pacing (A-pace) at the expiration thereof or may take the form of a V—V escape interval, initiated on ventricular sensing (V-event) or pacing (V-pace) and triggering ventricular pulse pacing (V-pace) at the expiration thereof. Digital controller/timer circuit 330 similarly defines the A-V delay intervals SAV and PAV that commence following a sensed A-event and a delivered A-pace, respectively. The specific values of the intervals defined are controlled by the microcomputer circuit 302 by means of data and control bus 306 from programmed in parameter values and operating modes.

Digital controller/timer circuit 330 also defines time intervals for controlling operation of the atrial and ventricular sense amplifiers in sense amplifier circuit 360. Typically, digital controller/timer circuit 330 defines an atrial blanking interval following delivery of an A-pace pulse, during which atrial sensing is disabled, as well as ventricular blanking intervals following atrial and ventricular pacing pulse delivery, during which ventricular sensing is disabled. Digital controller/timer circuit 330 also defines an atrial refractory period (ARP) during which atrial sensing is disabled or the A-event is ignored for the purpose of resetting the escape interval. The ARP extends from the beginning of the SAV or PAV interval following either an A-event or an A-trig and until a predetermined time following sensing of a ventricular depolarization or triggering the delivery of a V-pace pulse. Digital controller/timer circuit 330 similarly defines a ventricular refractory period (VRP), which is typically shorter than the portion of the ARP following ventricular sensing or pacing, following either a V-event or V-trig.

In the case of an ectopic V-event, both a VRP and a post-ventricular atrial refractory period (PVARP) defined by the digital controller/timer circuit 330 separately from the ARP may be generated. The durations of the ARP, PVARP and VRP may also be selected as a programmable parameter stored in the microcomputer 302. Digital controller/timer circuit 330 also controls sensitivity settings of the sense amplifiers 360 by means of sensitivity control 350.

In the embodiment illustrated in FIG. 3, the IPG 26 is provided with a piezo electric sensor 31 6 which is intended to monitor patient activity, in order to allow provision of DDDR rate responsive pacing, such that the defined pacing rate (A—A escape interval or V—V escape interval) increases with increased demand for oxygenated blood. Sensor 316 generates electrical signals in response to sensed physical activity which are processed by activity circuit 322 and provided to digital controller/timer circuit 330. Activity circuit 332 and associated sensor 316 may correspond to the circuitry disclosed in U.S. Pat. No. 5,052,388, issued to Betzold et al., and U.S. Pat. No. 4,428,378, issued to Anderson et al. incorporated herein by reference in their entireties. Similarly, the present invention may be practiced in conjunction with alternate types of sensors such as oxygenation sensors, pressure sensors, pH sensors and respiration sensors, or even combinations or multiples of these as they become more available for use in providing rate responsive pacing capabilities. As stated above, the present invention may also be practiced in non-rate responsive pacemakers.

Data transmission to and from the external programmer 40 illustrated in FIG. 2 is accomplished by means of the telemetry antenna 334 and an associated RF transmitter and receiver 322, which serves both to demodulate received downlink telemetry and to transmit uplink telemetry. For example, circuitry for demodulating and decoding downlink telemetry may correspond to that disclosed in U.S. Pat. No. 4,556,063 issued to Thompson et al. and U.S. Pat. No. 4,257,423 issued to McDonald et al., while uplink telemetry functions may be provided according to U.S. Pat. No. 5,127,404 issued to Wyborny et al. and U.S. Pat. No. 4,374,382 issued to Markowitz. Uplink telemetry capabilities will typically include the ability to transmit stored digital information as well as real time or stored EGMs of atrial and/or ventricular electrical activity (according to the teaching of the above-cited Wyborny patent), as well as transmission of Marker Channel pulses indicating the occurrence of sensed and paced depolarizations in the atrium and ventricle, as disclosed in the cited Markowitz patent.

In addition, in the context of the present invention, stimulation threshold data from a series of auto-capture test stimulation pace events may be stored in the RAM 310 or the RAM/ROM unit 314 of microcomputer 302 for later telemetry out on command of the programmer 40. Such testing can be done as is described in detail in the U.S. Pat. No. 5,601,615 patent or using any other capture detection and threshold testing system desired.

This data may be encoded in digital form and transmitted via RF transmitter 332 and antenna 334 to the external programmer 40 for display and/or analysis in the form of atrial and ventricular strength-duration curves described below with reference to FIG. 5.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexor circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexor 328, power-on-reset circuit 336 and crystal oscillator circuit 338 may correspond to any of those presently used in current marketed implantable cardiac pacemakers.

Microcomputer 302 controls the operational functions of digital controller/timer 324, specifying which timing intervals are employed, and controlling the duration of the various timing intervals, via data and control bus 306. Microcomputer 302 contains a microprocessor 304 and associated system clock 308 and on-processor RAM and ROM chips 310 and 31 2, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-trig, V-trig, A-event and V-event signals.

As described above, if the IPG is programmed to a rate responsive mode, the patient's activity level is monitored periodically and the escape interval is adjusted proportionally. A timed interrupt, e.g., every two seconds, may be provided in order to allow the microprocessor 304 to analyze the output of the activity circuit 322 and update the basic escape interval (A—A or V—V) of the IPG. The microprocessor 304 may also define variable A-V intervals and variable ARPs and VRPs which vary with the escape interval established in response to patient activity. For example, the microprocessor 304 may specify a variable rate adaptive decrement (RAD) interval to be subtracted from the defined A-V delay intervals when the heart rate (paced or sensed) is above a defined resting or "start" rate. Similarly microprocessor 304 may define ARPs and/or VRPs which decrease in duration in relation to an increase in sensed or paced heart rate above the start rate.

The illustrated IPG block diagram of FIG. 3 is merely exemplary, and corresponds to the general functional organization of most multi-programmable microprocessor controlled DDD(R) cardiac pacemakers presently commercially available. It is believed that the present invention is most readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microcomputer circuit 302. However, the present invention may also be usefully practiced by means of a full custom integrated circuit, for example, a circuit taking the form of a state machine as set forth in the above-cited Betzold et al. patent, in which a state counter serves to control an arithmetic logic unit to perform calculations according to a prescribed sequence of counter controlled steps. As such, the present invention should not be understood to be limited to a pacemaker having an architecture as illustrated in FIG. 3, and a circuit architecture as illustrated in FIG. 3 is not believed to be a prerequisite to enjoying the benefits of the present invention.

FIG. 4 is a functional flow chart of the normal operation of the pacemaker illustrated in FIGS. 1, 2 and 3 in DDD pacing mode. For the sake of simplicity, functional steps corresponding to the provision of refractory and blanking periods have been omitted, to allow for easier understanding of the overall operational mode. In the flow chart of FIG. 4, it is assumed that the basic timing of the device is based around of the definition of an atrial escape interval (A—A interval) which may be fixed or may vary as a result of the output of the physiologic sensor, e.g. the activity sensor 316 of FIG. 3 in a manner described above. (Other devices may use other intervals to time atrial paces such as, for example VA intervals, without undue experimentation from the description set forth here.) This A—A interval is reset at block 400, along with the current A-V delay intervals SAV and PAV(these are Sensed Atrial to Ventricular, and Paced Atrial to Ventricular intervals, respectively). During the A-V delay interval the device awaits either time out of the current A-V delay interval (PAV or SAV) at block 402 or ventricular sensing at block 406. If ventricular sensing (V-event) does not occur prior to A-V delay interval time out, a ventricular pacing pulse is generated at block 404 at the end of the A-V interval, and the values of the A-V intervals are updated, if necessary, at block 410.

If a ventricular depolarization or V-event is sensed at block 406, prior to expiration of the current A-V delay interval, the pacemaker's timing may optionally be reset at block 408 to deliver an atrial pacing pulse at a V-A escape interval (thereafter equal to the A—A escape interval minus the current A-V delay interval), or the device may proceed directly to updating the A-V delay intervals at block 410, and not alter the timing of the next scheduled atrial pacing pulse at the expiration of the A—A escape interval.

Following update of the base A-V delay interval at block 410, the device awaits expiration of the A—A (or optionally the V-A) escape interval at block 416, sensing of a ventricular depolarization at block 420 outside of the VRP, or sensing of an A-event at block 422, outside of the ARP. If the A—A (or V-A) escape interval expires at block 416 without any intervening A-event or V-event sensing, an A-pace pulse is generated at block 414, and the next succeeding A-V delay interval is defined to be equal to PAV at block 412, followed by reset of the A—A escape interval and the A-V delay interval at block 400.

In the event that a V-event is sensed at block 420 prior to expiration of the A—A escape interval, the timing is reset to trigger A-pace at the expiration of the V-A interval (A—A escape interval minus PAV). A V-event sensed at this point is not effective to trigger an update of the SAV and PAV intervals.

If an A-event is sensed at block 422, prior to expiration of the A—A (or V-A) interval, the subsequent A-V interval is defined to be equal to SAV at block 424, and the A—A escape and A-V delay intervals are reset at block 400.

In the normal, everyday operation of the IPG, the A-pace and V-pace pulse energy in each case may be established initially by programming the pulse widths and amplitudes post-operatively or at a later patient examination, generally called a pacemaker follow up. These settings can be accomplished by the devices described as programmers and PSA's illustrated in FIGS. 1 and 2. The programmed values are later, in a preferred practice of the present invention, periodically adjusted automatically so that the normal values may fluctuate from the programmed values.

The other time interval values, including the A—A escape interval, the PAV delay interval, the ARP, VRP and any other time intervals defined by operating algorithms at any particular time are stored in either ROM or RAM and are fetched and used as described with reference to FIG. 4. Thus, in the operations of the IPG in either the general algorithm of FIG. 4 or in the strength-duration (SD) algorithms described below, the specified time intervals may be fetched and employed in each designated step in response to the trigger or event signals designated in any of the algorithms.

PART II. CAPTURE DETECTION AND THRESHOLD MEASUREMENT.

Details of the stimulation threshold measurement and capture restoration features of the first aspect of the present invention incorporated into a dual chamber pacemaker of the type described above and of the second aspect of the invention incorporated into a single chamber pacemaker or the single chamber of a dual chamber pacemaker follow below. First the S-D (Strength-Duration, of the energy pulse) characteristics taken into account in the operation of the invention are described in reference to FIG. 5.

Figure 5:
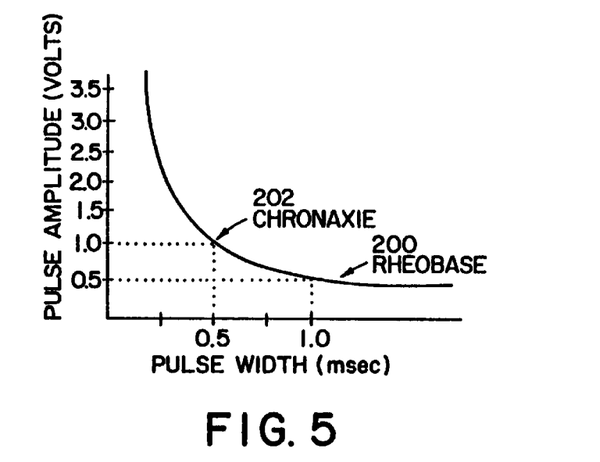
FIG. 5 is a graph of a typical strength-duration curve for cardiac stimulation signals.

FIG. 5 shows a typical S-D curve for electrical stimulation of myocardial tissue plotted as pulse amplitude in volts versus pulse width in milliseconds corresponding generally to FIG. 2 of the above-referenced '643 patent. The graph shows, inter alia, that the stimulation threshold increases with a decreasing pulse width, and thus decreases with an increasing pulse width, except that beyond the Rheobase 200, no further reductions in the amplitude threshold can be achieved. Thus, increasing the pulse width beyond about one millisecond (in the example shown) still requires a threshold of 0.5 volts. Also included on the graph for illustrative purposes is the Chronaxie 202, a measure of myocardial excitability, which is the point representing the lowest pulse width needed to have an amplitude threshold equal to twice the Rheobase threshold.

It is well known in the art to provide a safety margin between the actual delivered pacing pulse width and amplitude and the stimulation thresholds appearing in the strength-duration curve. However, as previously stated, the amount of the safety margin may change over time and must be balanced against the need to maximize battery life, as increased amplitude and pulse width will cause a greater battery energy consumption. Physiological changes in the patient may alter the thresholds from the initial programmed value or values, and can lead to loss of capture, with inadequate amplitude or pulse width.

PART III DESCRIPTION OF ATRIAL CAPTURE ENHANCEMENTS AND THEIR IMPLICATIONS.

In the preferred embodiment, the system requires that the pacemaker or PSA provide backup ventricular pacing at a rate equal to the test rate, as necessary, upon demand. In order to provide the flexibility to overdrive any encountered sinus rate, the programmable atrial rate range for the pacing threshold test should be 90–200 ppm. In doing so, ventricular backup support is ensured at a reasonable rate ranging from 45–100 ppm, at 2:1 A:V rates.

The simplest way to provide the invention's backup ventricular pacing operation is by switching between DDI and ADI pacing modalities on alternate sequences (FIG. 5). A specific test mode could alternatively be used that also could provide the functions this simple beat -by- beat mode switch can accomplish. Accordingly the simple approach is currently preferred because it can easily be integrated into current IPGs with little design effort, just programming changes.

Figure 10:
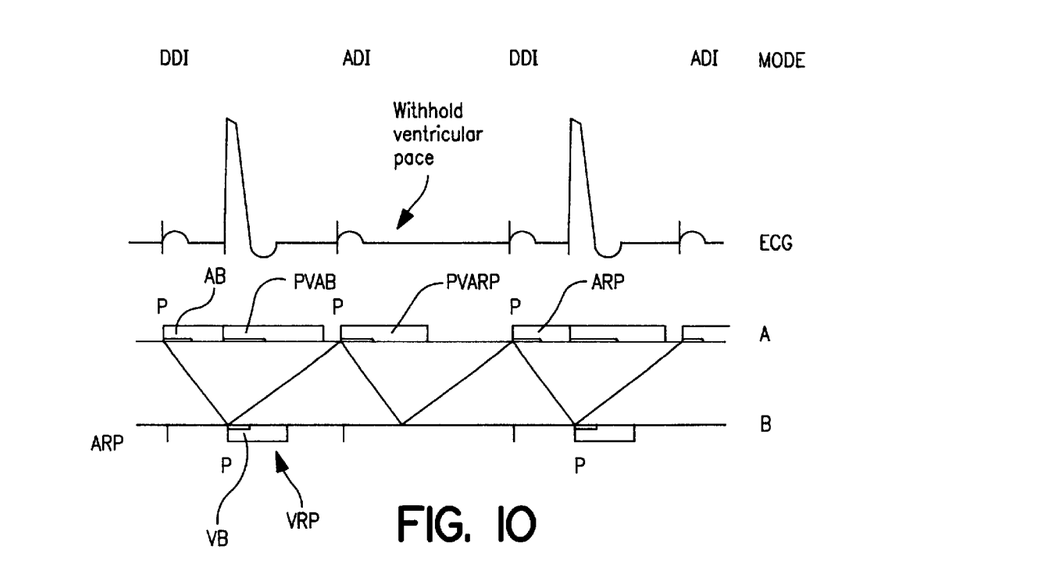
FIGS. 10–14 are each stylized illustrations of an ECG with temporary coincident Atrial channel (A) and Ventricular channel (V) pacemaker event timing diagrams.
Figure 11:
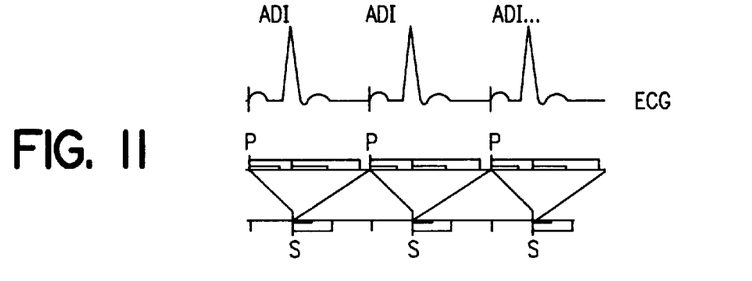

Refer now to FIG. 10 in which the timing or temporal correspondence of the operating mode, ECG and channel A and B events are illustrated. (In general these FIGS. 10–14 assume 100 msec post-atrial, and 150 msec post-ventricular atrial blanking, but alternative values can be used.) While operating in the ADI mode, should a ventricular sense occur prior to an atrial paced (or sensed) event, the pacemaker will: (1) initiate ventricular blanking (VB) and refractory (VRP) periods, and (2)initiate post ventricular atrial blanking (PVAB) and refractory (PVARP) periods, and (3) postpone the mode switch to DDI.

Thus, in the presence of intact atrioventricular (AV) conduction, even if it is prolonged, the pacemaker will maintain operation in the ADI mode by continually (and indefinitely) postponing a mode-switch to DDI because of the sensed ventricular event S, which in Apace/Dual sense/inhibited mode, stops the mode switch to Dual chamber/Dual sensor mode. This is seen clearly in the operation of the pacemaker in FIG. 11.

Figure 12:
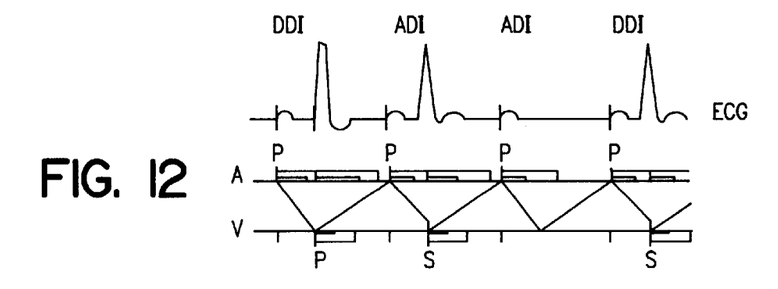

To illustrate the manner in which the IPG should operate in accord with this invention reference should now be had to FIG. 12. Here mode-switch back from ADI to DDI will occur in the event that a V-sense (ventricular sensed event) does not occur following the atrial pace. This indicates that AV conduction did not occur.

Also illustrated in FIG. 12 is while operating in the DDI mode, should a ventricular sense occur within the programmed paced AV (PAV) interval following an atrial pace, the pacemaker will inhibit the ventricular output and initiate atrial and ventricular blanking and refractory periods (as is normal in DDI pacemaker operation). The ventricular sense will not affect the timing of the succeeding atrial pace (per normal A—A timing operation).

Figure 18:
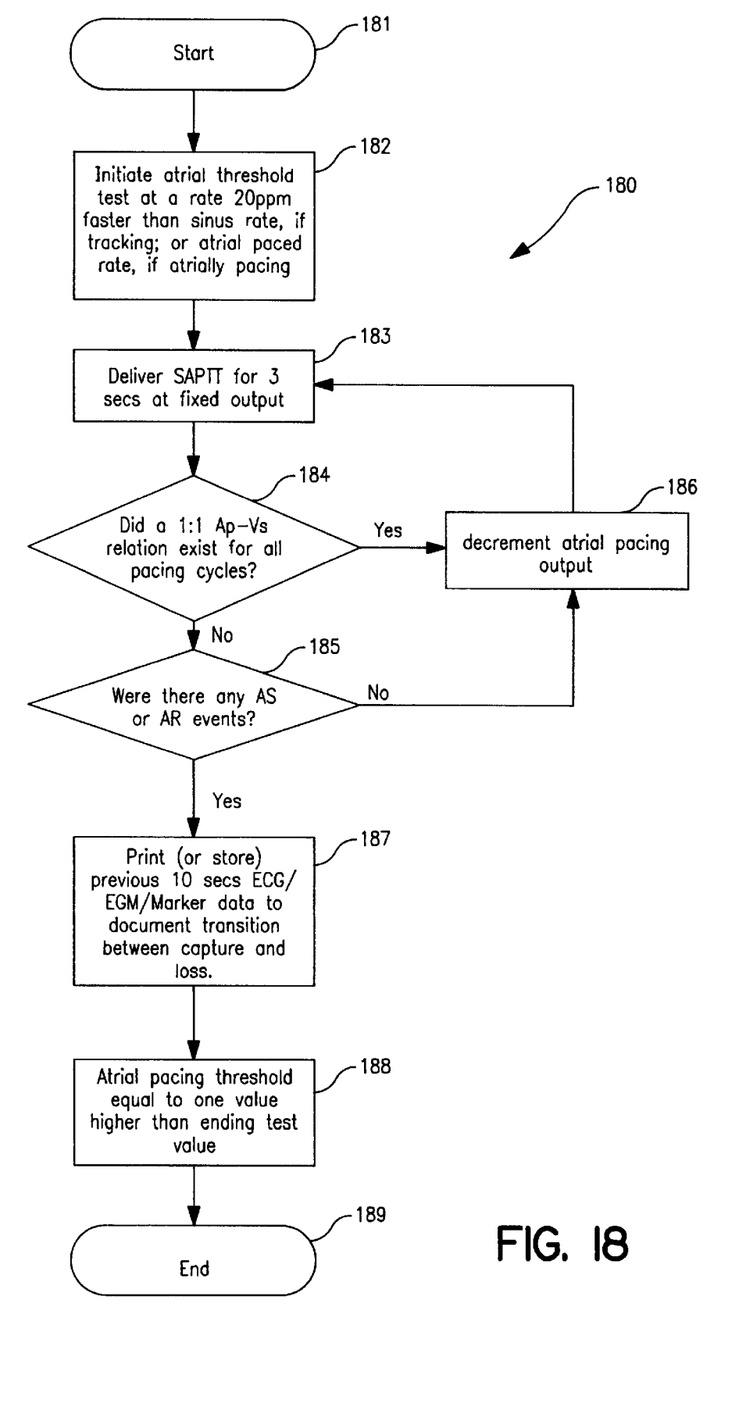
FIGS. 18 and 19 are flow charts.
Figure 19:
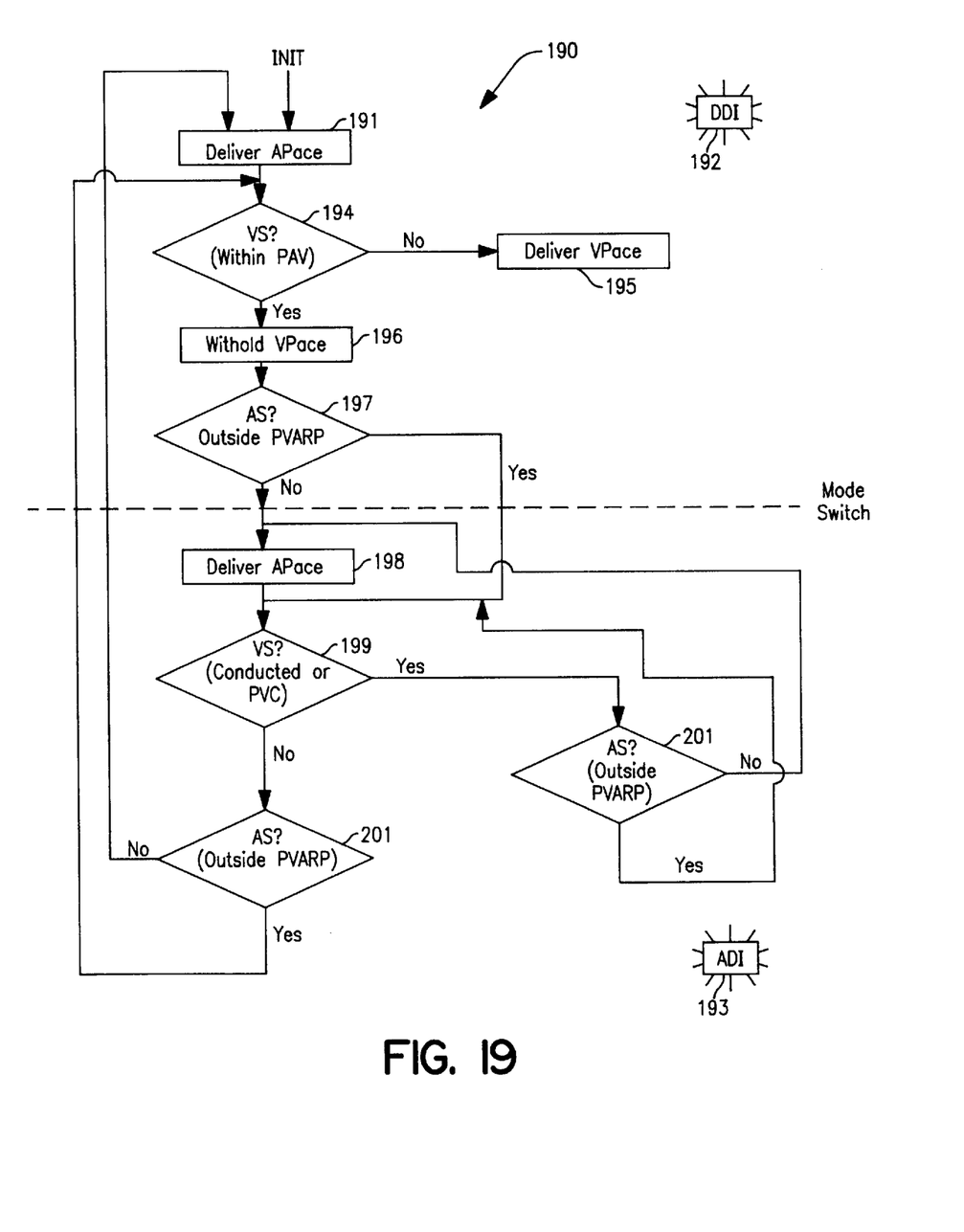

FIG. 18 provides an illustration of how the FAPTT (Facilitated Atrial Pacing Threshold Test) can be applied to autothreshold testing. FIG. 19 provides an illustration of the operational details of the FAPTT. Please refer to them in the following DISCUSSION section for their detail.

Certain safety features can be added to this basic program to handle cases of sick sinus syndrome and other abnormalities, but such enhancements can be added without inventive effort as thresholding programs are well understood. Such enhancements can be related to delivering a safe ventricular pace at 110 milliseconds should a ventricular sense occur outside the permanently programmed post atrial ventricular blanking period (PAVB) but within 110 milliseconds following an atrial pace delivered in the DDI mode; or for premature ventricular contraction (PVC)

Operation while in the DDI mode, a ventricular sense occurring outside the ventricular refractory period will:
1. not affect timing of the mode switch to ADI.
2. restart the ventricular blanking and refractory periods (but not beyond the scheduled A-pace).

Additional enhancements can be made as follows. Noise reversion should not apply during the 2:1 pacing threshold test. Notice that in general the ratio of atrial pacing rate to ventricular pacing rate is 2 to 1 while running the testing program. The program may of course be running in the pacemaker as described with reference to FIGS. 1 and 2, and external PSA and/or programmer. The ECG and AEGM tracings may be made by an additional piece of equipment if desired, by the programmer, by an enhanced PSA like the one in FIG. 1 or any means desired, including storage of the ECG or EGM data by the implanted IPG itself, for later telemetry out and playback or for telemetry out and playback concurrent with the test. Data from the ECG can of course be telephoned to distant sites for concurrent review by a supervising physician if desired, while the test is run or for storage and later retrieval.

In premature atrial contraction(PAC) Operation: Should an atrial sensed event occur outside of the post-ventricular atrial refractory period (PVARP) while operating in either the DDI or ADI mode, the pacemaker will:
1. start the appropriate post-atrial refractory and blanking periods,
2. switch to the appropriate mode after the scheduled atrial pace (This being illustrated in FIGS. 13 and 14),
3. restart the A—A timing interval after the scheduled atrial pace, and
4. restart the PAV after the scheduled atrial pace if switch to the DDI mode.

Figure 13:
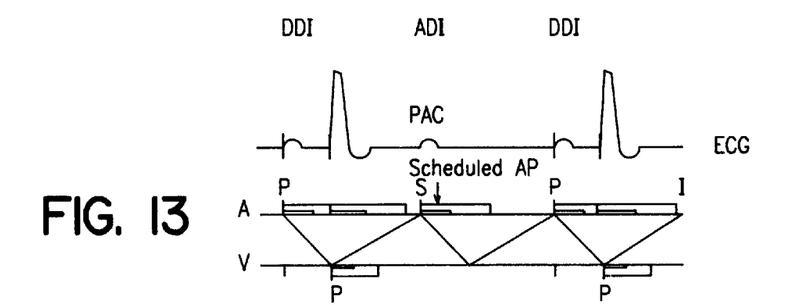
Figure 14:
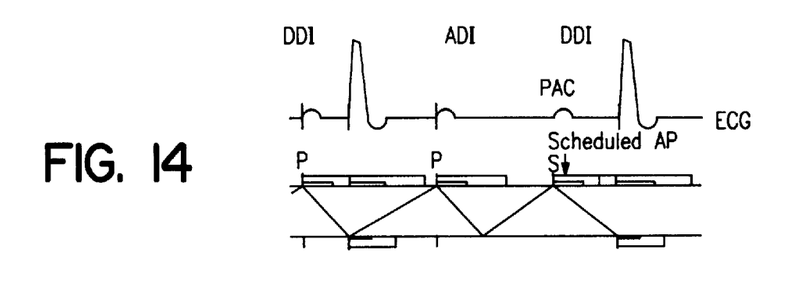

(FIGS. 13 and 14 show: Switch to ADI upon PAC, and Switch to DDI upon PAC, respectively.)

ANIMAL EXPERIMENT RESULTS.

Figure 15:
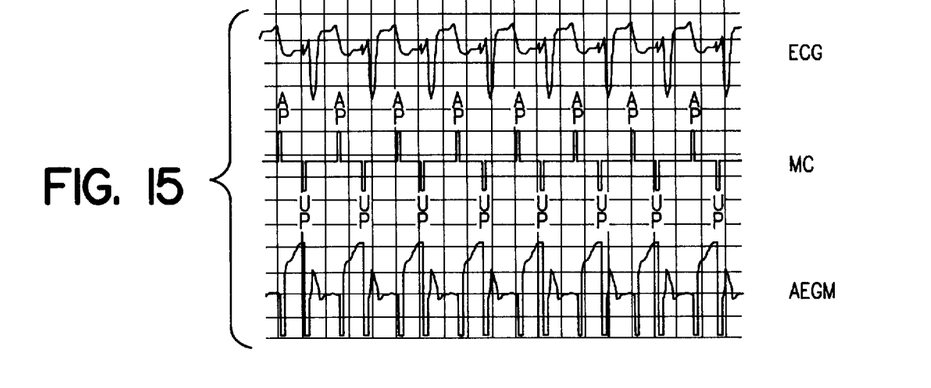
FIGS. 15–17 each illustrate a surface ECG and a temporally coincident marker channel recording and a temporary coincident intracardiac atrial electrogram (AEGM).
Figure 16:
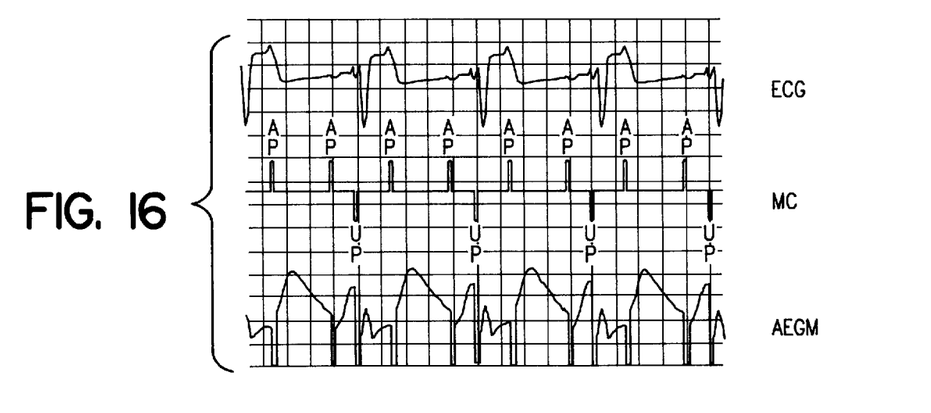
Figure 17:
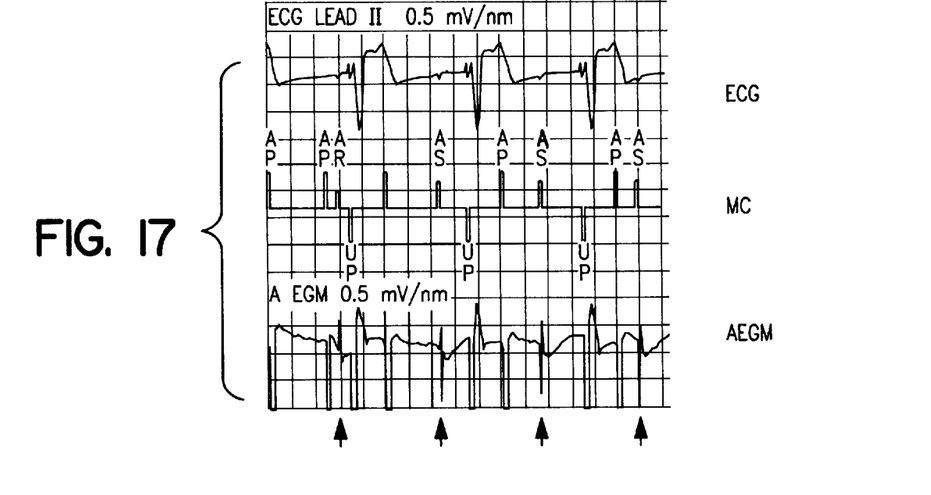

An early iteration of the inventive algorithm has been tested in two animals with induced complete heart block and sinus tachycardia. Illustrated in FIGS. 15 and 16 are the results from one of the animal experiments. Note the degree of difficulty difficult in visualizing atrial capture during 1:1 pacing due to overlap of the terminal portion of the preceding ventricular paced QRS complexes (FIG. 15). In this example, atrial capture assessment was greatly facilitated by providing ventricular support at a rate equal to ½ the atrial paced rate. In doing so, ECG isoelectric time was increased thereby facilitating visualization of atrial capture following alternating atrial paced events (FIG. 16, which is an ECG/Marker/AEGM strip taken during 2:1 AV pacing at an (atrial) rate of 120 ppm.).

DISCUSSION

The atrial pacing threshold test described herein allows the clinician to quickly and safely initiate atrial pacing threshold testing in dual chamber pacemaker patients regardless of their atrioventricular conduction status and without concern to their degree of pacemaker dependence. In patients with intact atrioventricular conduction, the presently preferred threshold test operates in the ADI pacing mode. By continually postponing a mode switch to DDI. Hence, the test will appear as it were being performed in the (preferred) AAI mode, thereby allowing the clinician to deduce atrial capture by the presence or absence of ventricular response.

In pacemaker dependent patients, ventricular support is assured throughout the duration of the test at a rate equal to ½ the atrial paced rate. In doing so, ECG isoelectric time is increased, thereby providing for better visualization of atrial capture following alternate atrial paces while overdrive pacing at higher rates. Moreover, 2:1 A-V pacing maintains ventricular pacing support at a safe and reasonable rate.

IMPLICATIONS FOR A PACING SYSTEM ANALYZER:

According to current practice, in patients having complete heart block and pacemaker dependence, atrial pacing thresholds are typically performed with the Model 5311 (B) (Trademark of Medtronic, Inc.) pacing system analyzer (PSA) operating in AAI (or AOO)mode while providing support via a separate external temporary pacemaker. A pacemaker system programmer/PSA as described above, with reference to FIGS. 1–3 could also perform this task.

Electrocardiographic visualization of atrial capture during ECG isoelectric periods is facilitated by programming the temporary ventricular pacemaker to a relatively slow pacing rate (e.g. <40 ppm). The inventive atrial pacing test offers the advantages of: 1) promoting quick interpretation of atrial thresholds by providing for fixed timing between atrial and ventricular events so that atrial paces are consistently delivered during isoelectric ECG periods., and, 2) provides a hemodynamic benefit and reduces the potential for pacemaker syndrome by maintaining appropriate atrioventricular timing, and, 3) obviates the need for a separate external pacemaker and coordination with a 2nd operator.

IMPLICATIONS FOR PERMANENT PACEMAKERS:

In patients having permanent pacemakers, the proposed atrial pacing threshold test safely provides for ease of use and the potential for reduced pacemaker follow-up time in all patients. According to present practice, a clinician will typically either 1) establish whether a given patient has intact conduction (or an underlying ventricular escape rhythm) before performing a pacing threshold test in the (preferred) AAI mode, or 2) perform the test in the DDD mode. Some more experienced clinicians will cautiously proceed to the AAI mode without pre-checking for an underlying rhythm.

The inventive Facilitated atrial pacing threshold test (FAPTT) allows one to safely forgo having to pre-check for an underlying ventricular rhythm as ventricular support is assured. In patients with intact atrioventricular (A-V) conduction, the test executes in the preferred ADI mode which allows for quick determination of atrial capture by simply observing the ventricular response. In patients without A-V conduction and an elevated sinus rate (e.g. such as in pediatric applications), 2:1 AV pacing allows overdrive pacing without overcrowding the ECG. Moreover, in sick elderly patients with heart failure and coronary disease, the FAPTT allows overdrive atrial pacing while simultaneously maintaining a safe and reasonable ventricular heart rate, i.e. below the patient's ischemic threshold.

IMPLICATIONS FOR AN AUTOMATIC THRESHOLD TEST:

In addition to abetting ECG capture visualization, the FAPTT algorithm carries important implications for automatic atrial threshold determination. As discussed previously, inferences of atrial capture (or loss thereof) are often made based on evidence of either 1:1 AV conduction, or alternatively upon the appearance of native p-waves. It would therefore be quite straightforward to apply the rules that are currently being used by humans to a pacemaker algorithm. Moreover, in cases when native p-wave sensing is necessary to determine loss of atrial capture, the elimination of post-ventricular blanking periods on alternating sequences via 2:1 pacing provides for enhanced pacemaker visualization of native atrial depolarizations (refer to FIG. 5). For instance at an (atrial) paced rate of 120 ppm, total atrial blanking during 1:1 pacing consumes 50% of the pacemaker's atrial alert time versus 35% when pacing 2:1.

ADAPTATION OF THE TEST PROCEEDURES

Although the details of how the test may be applied may vary depending on the equipment used, the brand of IPG, and so forth, the general structure of the testing process should comply with the description of the flow charts of FIGS. 18 and 19.

Most possible situations are outlined with reference to FIGS. 10–14 for the Facilitated Atrial Pacing Threshold Test(FAPTT). In FIG. 18 a program flow chart 180 starts at step 181 with a call to it by a user, in the case of implant or follow-up, or by the IPG itself if atrial threshold testing is done automatically. If the physician during implant or follow up is running the test directly, she may do so by a direct invocation of the test for as long as she likes, rather than a predetermined time as suggested n Step 183. The reader may set up the PSA and external pacing device or the programmer to run the program to operate substantially as shown in FIG. 19 for the physician with any user interface desired.

In FIG. 18, for automatic initiation, the pacing rate is boosted from the current sinus rate or the atrial pacing rate if pacing in step 182. This boosting or rate increase when there is a sinus rhythm reduces the likelihood of atrial events occurring before the pace pulse is delivered. Then we begin the FAPTT in step 183, whether in automatic or physician assisted mode. Either way the atrial pacing rate should be increased if you are not tracking sinus rhythms.

Referring to FIG. 19, then, we start with step 183a. After being initiated and a timer started for a predetermined time, (such as the three seconds suggested in step 183), or after being initiated by a physician activating his interface and continuing until he deactivates it, the program 190 sets the IPG into DDI mode 192 (here shown as being in the area of the diagram sharing or on the same side as the DDI icon 192) and then delivers an A-Pace in that mode(step 191). Step 194 is a monitoring step wherein the system looks for a Ventricular sense (VS) within the time for the paced AV interval to time-out. If it reaches the time-out before sensing a VS then it delivers a V-Pace (195) otherwise it witholds the potential V-Pace 196 and checks for and atrial sense (AS) outside the period defined by PVARP 197. If there's an AS it lets the next scheduled A-Pace time go by without delivering an A-Pace and checks for a Ventricular Sense VS in step 199. However, in moving from step 197 to 198 or 199, the program changes mode settings to ADI mode, indicated here by icon 193 on the ADI side of the dotted line. If there is a VS in step 199's time of monitoring, a second criteria should be examined, checking for an AS outside PVARP, step 201 If one (AS) is detected in step 201, the program stays in the ADI mode and checks again for a VS. (This follows as logical because it means there was a likelihood of AV conduction so there's not reason to switch back to DDI mode). Also, if there was no VS detected in step 199, the program checks for an AS outside PVARP, but then in either case it switches back to the DDI mode, delivering an A-Pace if one is needed, or just checking for the next VS in step 194.

FIG. 18, and the main or automatic atrial test program continues from there. If there were no non-conducted atrial paces, step 186 lowers the threshold, if there were, and there was breakout of sinus events (185) the threshold is presumed found, and the program moves to steps 187 and/or 188 depending on whether we are doing the test in an automatic mode and how much information we want to retain, but if there was no breakout, the test threshold can be lowered again (186). so that the minimum required atrial pacing energy may be iteratively discovered.

While many reasonable variations and improvements may be made to this invention, it is only limited in scope by the following amended claims.

What is claimed is:

1. A test for atrial capture and thresholding comprising the following steps:

determining whether a patient has evidence of heart block, if the patient has no evidence of heart block, enabling the monitoring of ventricular sensed events and starting atrial capture detect and threshold testing and operating such testing until capture and threshold energy levels for atrial test pulses are adequately determined, adjusting atrial pace pulse energies to reflect the adequately determined capture and threshold energy levels, and if there is evidence of patient heart block, decreasing the pacing rate for ventricular support to substantially less than the atrial rate, then starting atrial capture detect and thresholds, and operating such testing until capture and threshold energy levels for atrial test pulses are adequately determined, adjusting atrial pace pulse energies to reflect the adequately determined capture and threshold energy levels.

2. The method as set forth in claim 1 wherein said method steps are initiated automatically under control of an implanted device upon the occurrence of predetermined criteria and terminated automatically when said thresholds are adequately determined.

3. The method of claim 1 further comprising recording an electrocardiogram during the testing.

4. The method of claim 2 further comprising recording an electrocardiogram during the testing.

5. A system for facilitating atrial capture detection and for generating energy level and timing values for pacing an atrium of a living heart during a test, said system having means adapted to receive inputs indicating atrial and ventricular events and having pacing leads electrically associated with an atrium and ventricle of the heart and having storage for a program for signaling a pulse generator to deliver pacing pulses to said ventricle at a rate near ½ the rate of atrial pacing during said test.

6. A system as set forth in claim 5 wherein said leads are said means adapted to receive said inputs indicating said atrial and ventricular events.

7. A system as set forth in claim 5 wherein said system further comprises:

external user interface means for allowing a user to initiate operation of said program, and for determining the end of said program operation.

8. A system as set forth in claim 5 wherein said system further comprises:

recordation means for displaying electrogram traces to a user of a patient electrogram during the time said program is in operation.

9. A system as set forth in claim 5 wherein said system further comprises:

storage means for storing data representative of electrogram tracings so as to enable display of such data in user readable form for a user.

10. A system as set forth in claim 5 wherein said system further comprises:

an additional program for automatic initiation of said program upon the occurrence of a predetermined event.

11. A system as set forth in claim 5 further comprising telemetry means addressable by said program wherein said program produces output signals to operate an implanted IPG's pacing functions by telemetericaly delivered commands.

12. A system as set forth in claim 5 wherein said program operates by switching an implanted IPG from DDI to ADI on a first operation and then only switches back to DDI on the non occurrence of a VS event.

13. A system as set forth in claim 5 further comprising a programmer having electrodes for connections to a patient's skin and for sensing an ECG therefrom, wherein said programmer monitors and displays an ECG while said program is in operation.

* * * * *